United States Patent [19]

McCutcheon

[11] Patent Number: 4,909,413

[45] Date of Patent: Mar. 20, 1990

[54] METHOD OF AND APPARATUS FOR DISPENSING RUBBER GLOVES IN AN ASEPTIC CONDITION FOR INSERTION OF THE HANDS OF A USER

[75] Inventor: Raymond L. McCutcheon, Charleston, W. Va.

[73] Assignee: Medical Implements, Inc., Richmond, Va.

[21] Appl. No.: 299,065

[22] Filed: Jan. 19, 1989

[51] Int. Cl.$^4$ .......................................... B65H 16/00
[52] U.S. Cl. ........................................ 221/1; 221/25; 221/71
[58] Field of Search ...................... 221/25, 26, 27–29, 221/70, 71, 63, 33, 45, 47, 56; 53/386; 206/69, 828; 248/99

[56] References Cited

U.S. PATENT DOCUMENTS

| | | | |
|---|---|---|---|
| 3,047,347 | 7/1962 | Groves | 221/25 X |
| 3,482,733 | 12/1969 | Groves | 221/25 |
| 3,502,244 | 3/1970 | Irvin | 221/63 |
| 3,798,870 | 3/1974 | Kanner et al. | 53/386 X |
| 3,855,757 | 12/1974 | Joseloff | 53/386 X |

FOREIGN PATENT DOCUMENTS 54-38889  3/1979  Japan ..................................... 53/386

Primary Examiner—Joseph J. Rolla
Assistant Examiner—David H. Bollinger
Attorney, Agent, or Firm—Richard P. Matthews

[57] ABSTRACT

A method of and apparatus for dispensing rubber gloves in an aseptic condition for insertion of the hands of a user. The gloves to be dispensed are contained within a chamber in a suitable housing provided with hand holes for a user. The gloves are attached to a continuous web of material provided with an aperture at each glove attachment for insertion of a hand of the user. Each glove is covered by a packaging film that is lightly perforated at each glove. The gloves are fed intermittently into registry with the hand holes in the housing. The user activates a vacuum pressure which is in fluid communication with the hand holes causing the gloves to expand and rupture through the film of packaging material. The user inserts his hands, deactivates the vacuum pressure, thrusts his hands further into the housing to detach a temporary retention of the gloves and removes his hands from the housing with the gloves aseptically applied.

11 Claims, 6 Drawing Sheets

METHOD OF AND APPARATUS FOR DISPENSING RUBBER GLOVES IN AN ASEPTIC CONDITION FOR INSERTION OF THE HANDS OF A USER

This invention relates to a method of and apparatus for dispensing rubber gloves aseptically, and, more particularly, to such a method and apparatus which uses vacuum pressure to expand and open the gloves for ease of insertion of the user's hands.

BACKGROUND OF THE INVENTION

Because of the recent increased awareness of communicable diseases, such as AIDS and Hepatitis B, all health care professionals are being encouraged to wear rubber gloves during patient contact procedures. In addition, people outside the health care industry are often required to wear rubber gloves while performing their duties on the job.

SUMMARY OF THE INVENTION

The apparatus of the present invention has been developed in order to make the process of putting on the gloves easier, quicker, and more sanitary. The apparatus utilizes a vacuum pump, the output of which is connected to two vacuum chambers the mouths of which are suitably sealed to two hand hole openings in the front of a housing for the apparatus. Right and left handed gloves are attached to two separate and parallel webs of material and fed intermittently to the hand hole openings. The vacuum pump may be activated and deactivated by any suitable means such as by a foot pedal actuated by the user. The negative pressure in the chambers causes the gloves to expand into the chambers so that the user's hands can be inserted fully. When the vacuum is released, the gloves conform to the hands of the user and with further insertion of the hands and/or a twist of the wrist, the user disengages a glove cuff holder at the mouth of each chambers.

The gloves themselves are packaged with the cuff on a frame member made of cardboard or plastic that fits the mouth of each chamber. The mouth may be surrounded with a rubber gasket or other means to ensure a sufficiently tight seal of the packaged glove during activation of the vacuum pump. A packaging film is placed over the glove and this film is lightly perforated vertically and horizontally at the locus of the hand holes so that the film will tear easily when the vacuum pressure is applied. The packages may also be marked from thumb position to allow for proper placement of the gloves in the chamber.

The gloves are fed intermittently under the control of the user by spring means, sprocket means, indexing means, or any other suitable means and may be combined with the foot pedal actuation of the vacuum pump. The vacuum in the chamber seals the glove onto the chamber mouth so that each glove may be expanded into its respective chamber whereby the gloving procedure may be completed. The next glove, when fed onto the mouth of the chamber, displaces the frame of the cuff holder of the preceding glove.

Gloving in the manner described in the present invention not only expedites the gloving procedure but also results in a tighter fitting glove and improves fingertip tactile sense. In large settings, such as hospitals, it may be advantageous to use a central vacuum system for the expansion of the glove in the chambers rather than an individual vacuum pump.

The inherent improvements and advantages of the present invention will become more readily apparent upon reference to the following detailed description of the invention and by reference to the drawings wherein.

DETAILED DESCRIPTION OF THE PREFERRED EMBODIMENT

Figure 1:
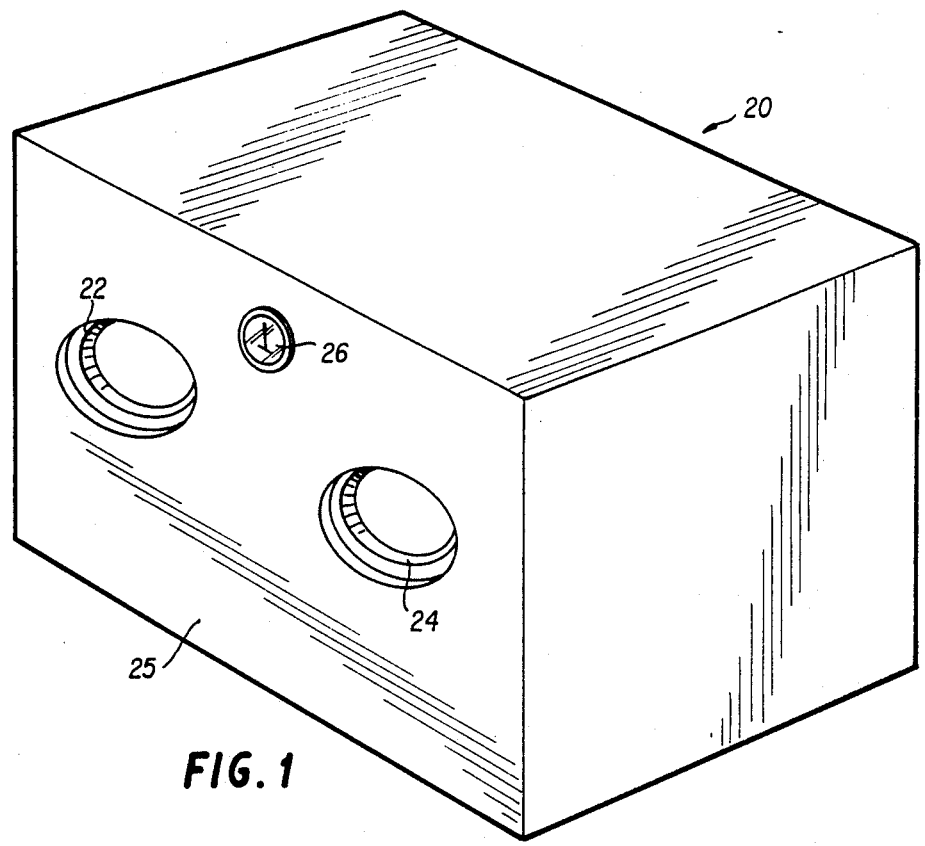
FIG. 1 is a perspective view of the housing used in the present invention.

Referring now to FIG. 1 of the drawings, there is illustrated a housing or cabinet indicated generally at 20, having a left hand hole 22 and a right hand hole 24 in the front face 25 thereof. A vacuum gage is shown at 26 to indicate a vacuum pressure that is provided for within the housing.

Figure 2:
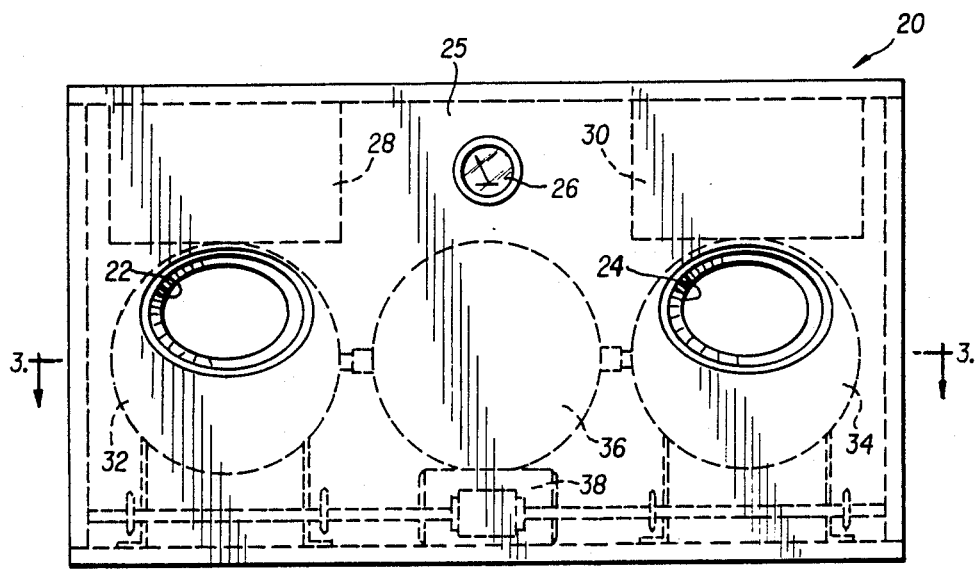
FIG. 2 is a front elevational view of the housing of FIG. 1.
Figure 3:
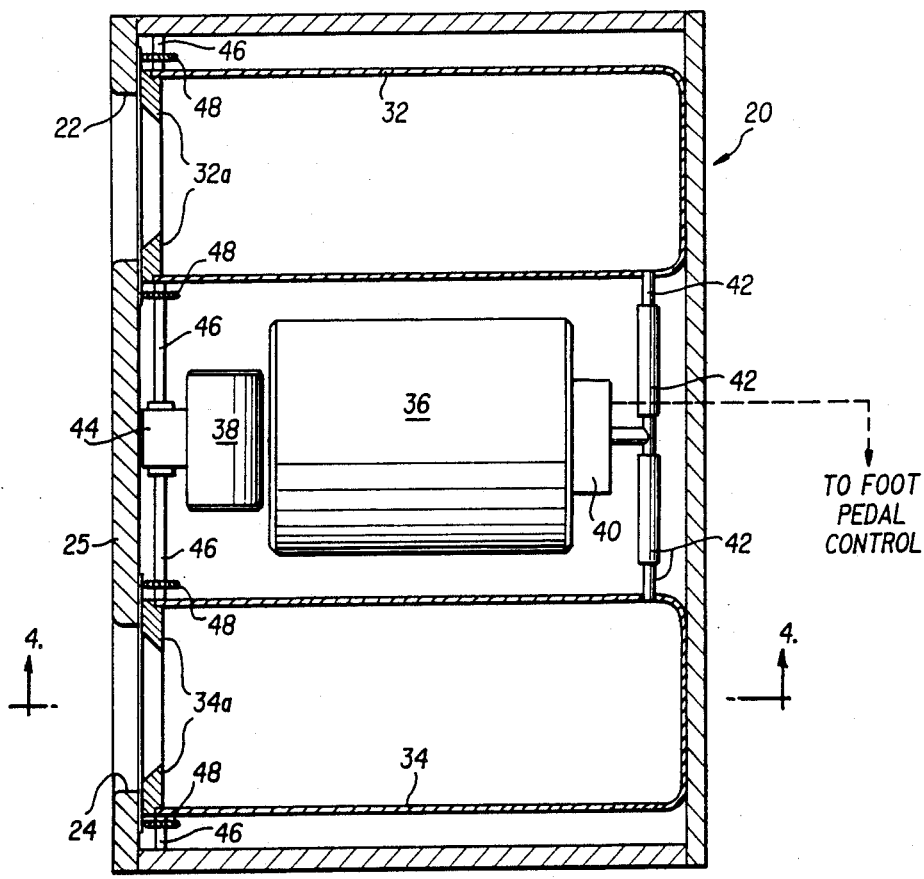
FIG. 3 is a plan view taken in horizontal cross section along line 3—3 of FIG. 2.
Figure 4:
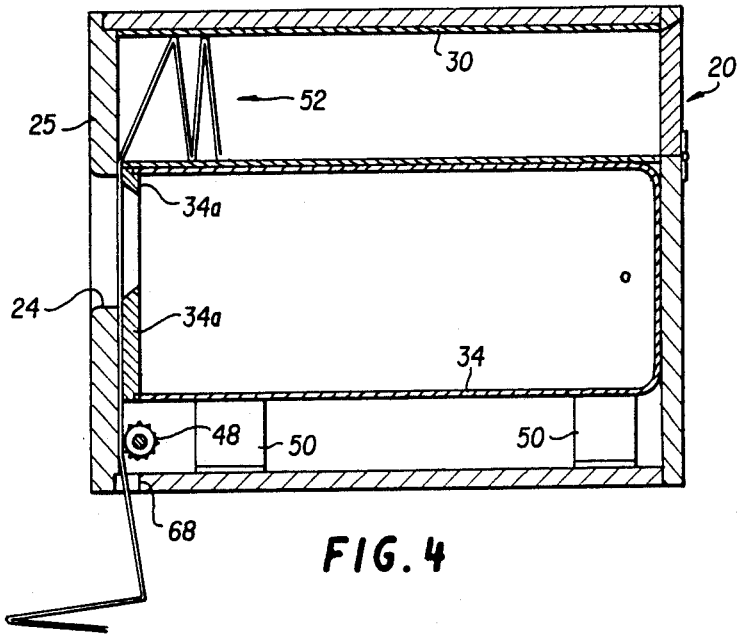
FIG. 4 is an elevational view taken in vertical cross section along line 4—4 of FIG. 3.

Reference to FIGS. 2-4 illustrate a compartment 28 within housing 20 for storing left hand gloves and another compartment 30 for storing right hand gloves. A vacuum chamber 32 has its top 32a placed in sealing relationship with respect to the left hand hole 22 and vacuum chamber 34 has its top portion 34a in sealing relationship with right hand hole 24. Rubber gasketing may be employed to ensure a tight seal around holes 22, 24 but the gasketing has been omitted from the drawings for ease of illustration.

Vacuum pump 36 is positioned centrally of the housing or cabinet 20 and supplies vacuum pressure through suitable tubing 42 to the vacuum chambers 32 and 34. A motor is shown at 38 for purposes of driving or feeding a web material containing the gloves as will be described hereinafter. Power supply 40 is provided with power from an external source, not shown, and may be connected to a foot pedal for purposes of controlling the vacuum pump 36 as well as the running of motor 38. Suitable reduction and right angle gearing is contained in gear box 44 to drive shafts 46 and thereby rotate drive sprockets 48. Any conventional drive means may be employed including spring feed means, Geneva indexing means, a single rotation clutch, or a sprocket and track means, which is illustrated. Vacuum chamber supports are shown at 50 in FIG. 4.

Figure 5:
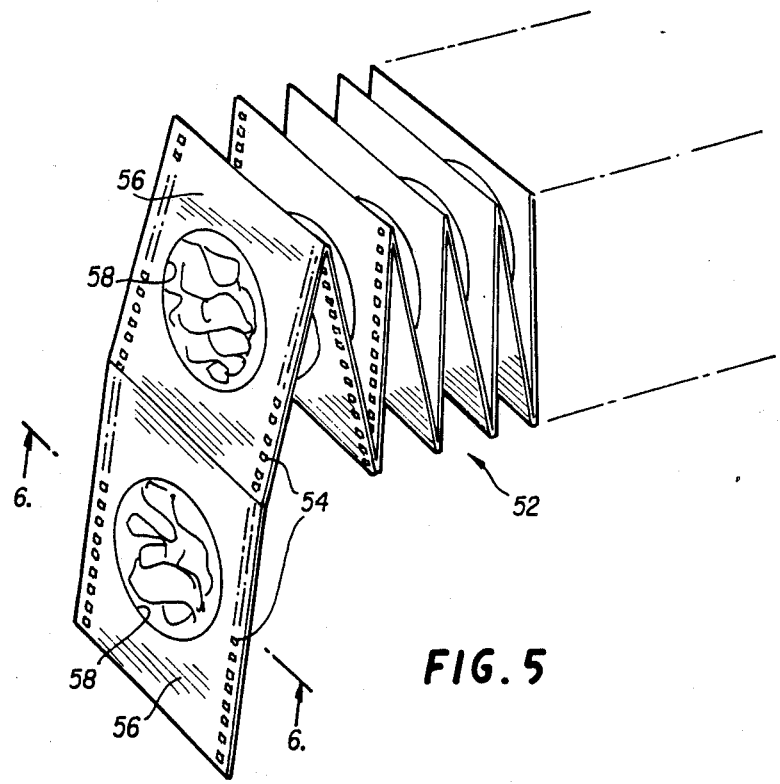
FIG. 5 is an enlarged, fragmentary perspective view of a glove carrying web material.
Figure 6:
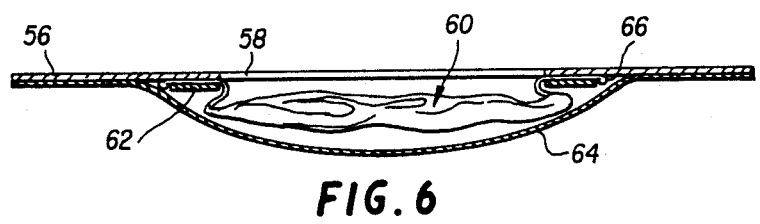
FIG. 6 is an elevational view taken in vertical cross section along line 6—6 of FIG. 5.
Figure 7:
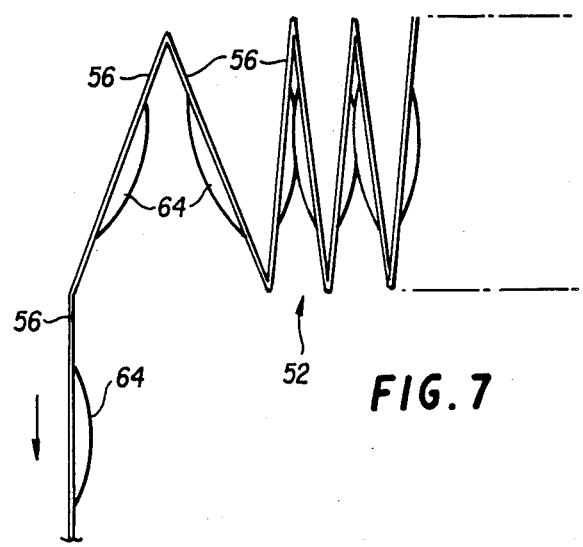
FIG. 7 is a side elevational view of the glove carrying web material of FIG. 5.
Figure 8:
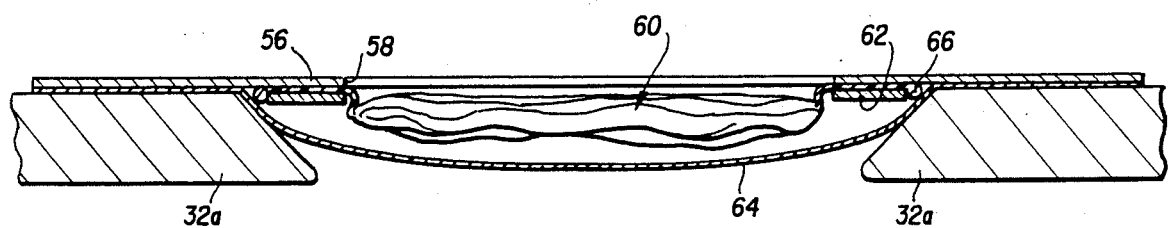
FIG. 8 is a fragmentary, schematic plan view taken in horizontal cross section showing a glove in dispensing position.
Figure 9:
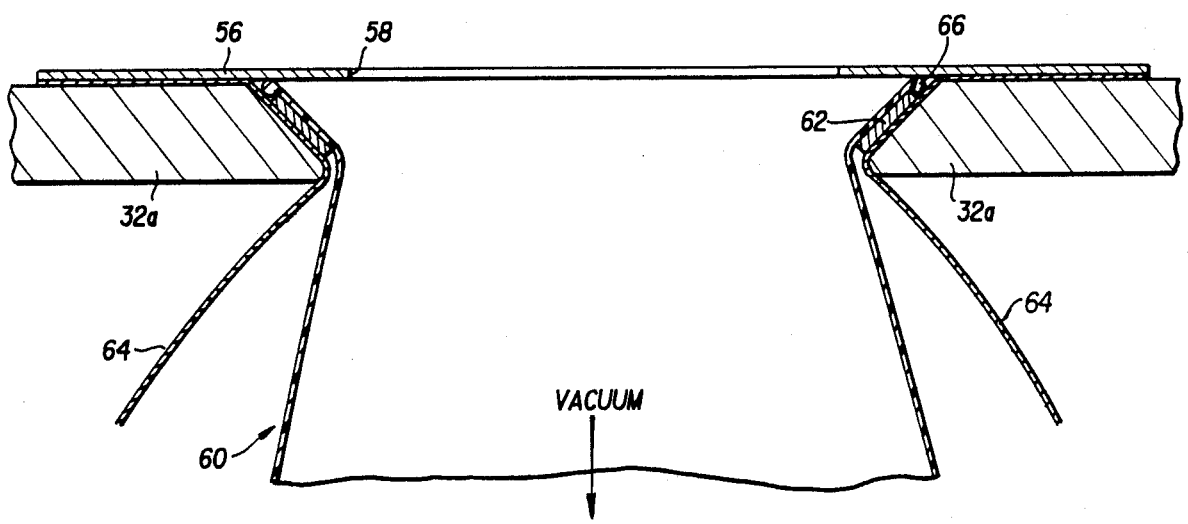
FIG. 9 is a fragmentary, schematic plan view taken in horizontal cross section showing the tearing of the packaging film when vacuum is applied.
Figure 10:
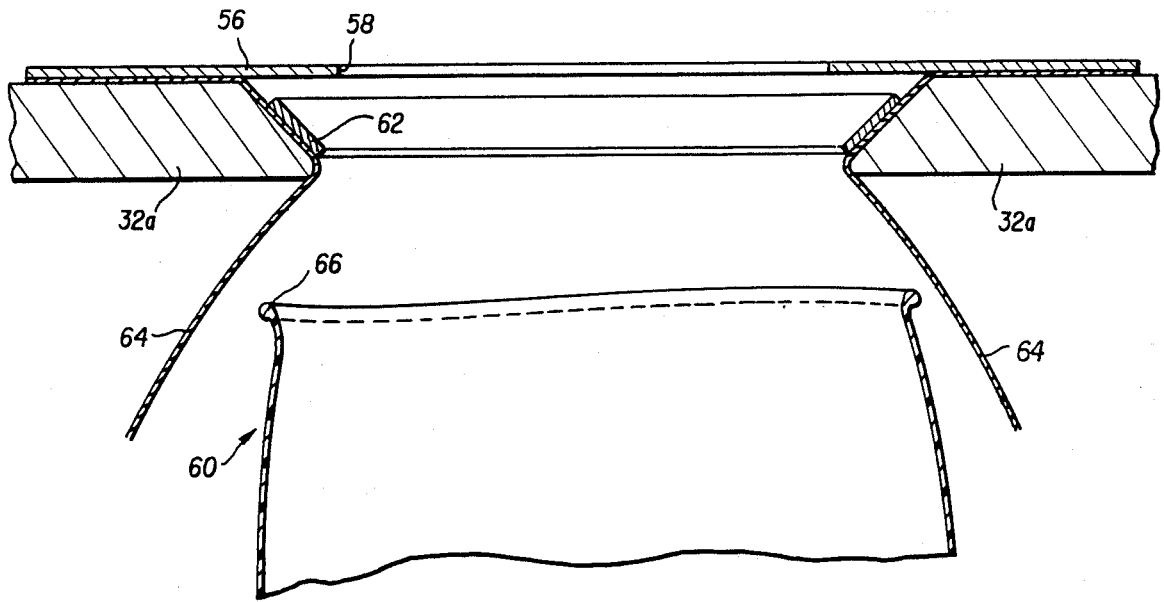
FIG. 10 is a fragmentary, schematic plan view taken in horizontal cross section showing the release of the glove.

Glove assembly packages are illustrated in FIGS. 5, 6 and 7. A frame means 56 for each individual glove is provided with perforations 54 which provide tracking means for sprockets 48 in order to feed the individual frame means into registry with hand holes 22, 24. Frame means are folded or corrugated as illustrated in FIGS. 5 and 7 in their stored position and when withdrawn from the individual compartments 28 and 30, form a web material for transporting the individual glove members. Each frame means 56 is provided with an opening 58 in its front face to permit passage of the user's hand which is inserted into an individual glove. Each glove is designated generally at 60 and is temporarily retained on the frame means 56 by means of an outer ring 62. A protective packaging material which may take the form of a plastic film 64 completes the package and helps to retain the glove in its original position. This packaging material 64 may be lightly perforated in the region opposite opening 58 though not specifically illustrated so as permit the packaging material to tear easily when the glove package is subjected to vacuum pressure. The rear portion of the cuff of the glove which is the point at which the user's hand is inserted into the glove, is provided with a raised bead 66 which is temporarily trapped and retained by outer ring 62 which functions as an abutment means.

Figure 11:
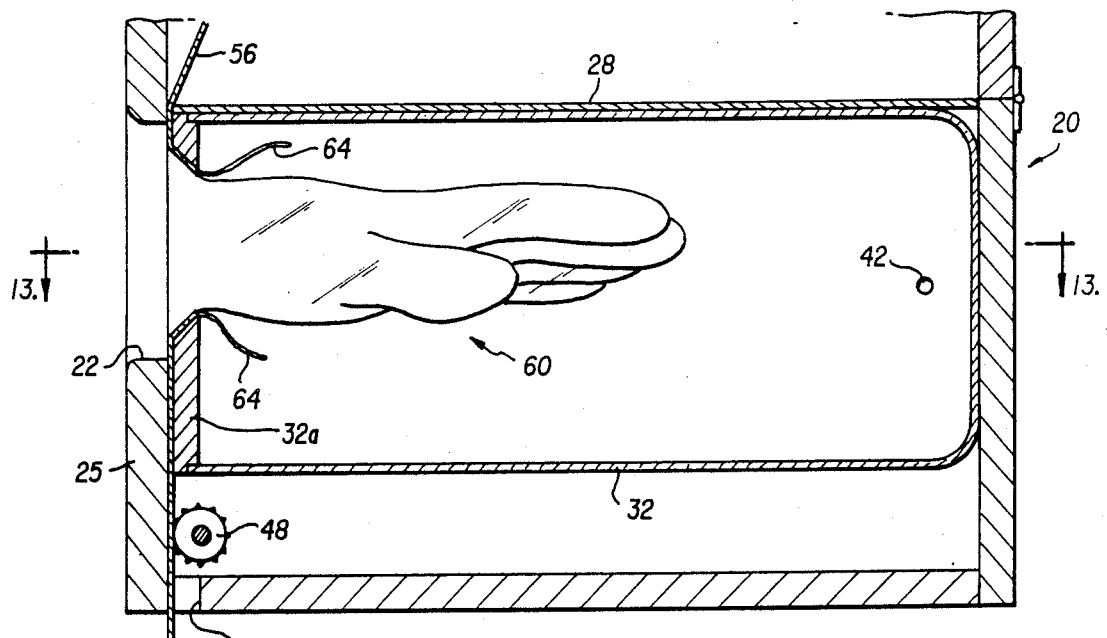
FIG. 11 is a fragmentary, schematic elevational view taken in vertical cross section showing the glove in expanded position.
Figure 12:
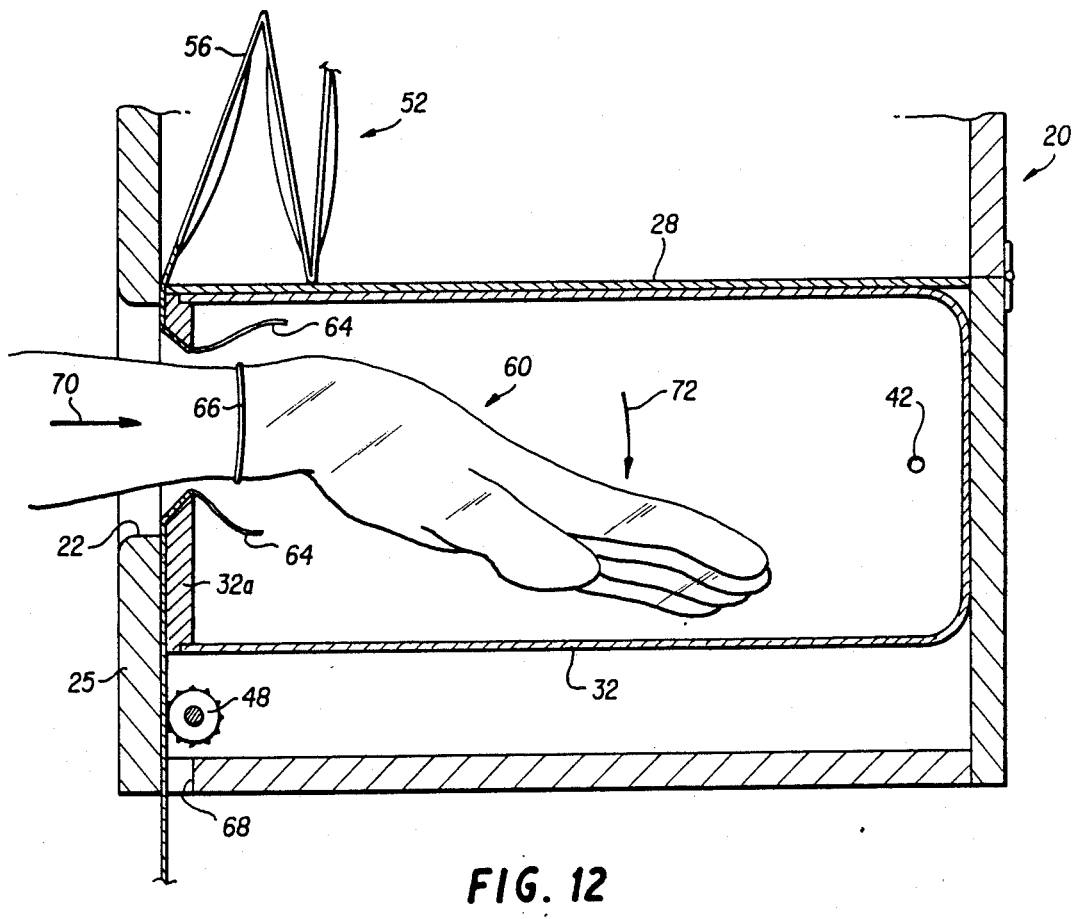
FIG. 12 is a fragmentary schematic elevational view taken in vertical cross section showing the inward thrust of the user's hand and twisting of the wrist to free the glove from its retained position.
Figure 13:
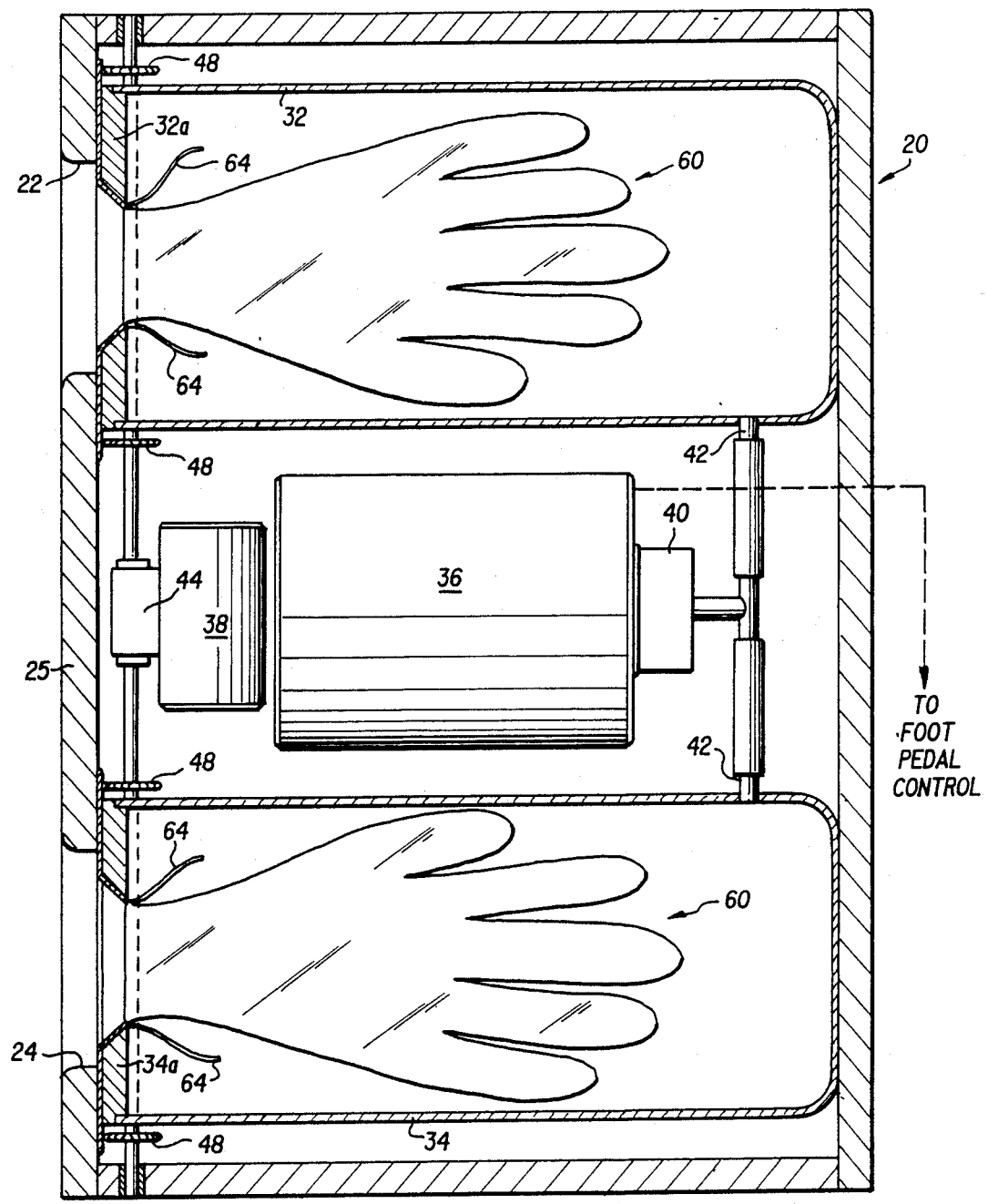
FIG. 13 is a schematic top plan view taken in horizontal cross section showing the left hand and right hand gloves in expanded position.

Reference is made to FIGS. 11-13 to illustrate the major method steps in the gloving process and further explain the operation of the apparatus. In FIG. 11, the gloves which are retained at regularly spaced locations along the web material and covered with packaging material 64 as illustrated in FIGS. 5-7, have been fed or indexed in order to position the glove, in this instance, a left hand glove, at the left hand hole 22. The user actuates the vacuum pump by means of a foot pedal to inflate and expand the glove which ruptures through the weakened plastic fill 64 to reach the position shown in FIG. 11 whereby it is possible for the user to insert his left hand into the glove. FIG. 12 shows how the user's hand is inserted into the glove and thrust further into the vacuum chamber in the direction shown by arrow 70 with a concurrent downward twisting of the wrist indicated by arrow 72. These motions permit bead 66 to clear the abutment provided by ring 62, thereby freeing the glove 60 and permitting the withdrawal thereof. The spent packaging material leaves the apparatus through a bottom exit port 68.

The plan view of FIG. 13 is comparable to the position shown in FIG. 11, and shows how both the left and right hand gloves are inflated simultaneously. When the user releases the vacuum pressure, the expanded glove collapses and conforms to the fingers, thumb and hand of the user. The slight over expansion that occurs during inflation ensures that the fingers and thumb can be fully inserted and improves fingertip tactile sense.

While the invention has been illustrated and described with respect to providing aseptic condition for the dispensing of gloves, it is possible to further refine the design to make it applicable to completely sterile conditions. However, for many clinical procedures aseptic, but non-sterile, conditions are acceptable.

While the invention has been illustrated and described with respect to preferred embodiments thereof, it will be recognized that the invention may be otherwise variously embodied and practiced within the scope of the claims which follow.

I claim:

1. An apparatus for dispensing rubber gloves in aseptic condition which comprises:
    a. a housing,
    b. a dispensing chamber within said housing for containing gloves to be dispensed in aseptic condition,
    c. hand hole means in said housing to admit the insertion of the hands of a user,
    d. means for introducing a vacuum within said housing in fluid communication with said hand hole means,
    e. and means for feeding gloves to be dispensed over said hand hole means,
        i. said vacuum within said housing effecting expansion of said gloves at said hand hole means.

2. An apparatus for dispensing rubber gloves in aseptic condition which comprises:
    a. a housing,
    b. a dispensing chamber within said housing for containing gloves to be dispenses in aseptic condition,
    c. frame means for transporting said gloves in a continuous web,
        i. said frame means including retaining means for temporarily retaining each glove to said frame means,
        ii. said frame means being provided with an aperture for each glove to permit a hand of a user to be inserted therethrough,
    d. hand hole means in said housing to admit the insertion of the hands of a user,
    e. means for introducing a vacuum pressure within said housing in fluid communication with said hand hole means, and
    f. means for indexing said frame means to position a glove retained on said frame means over said hand hole means,
        i. said vacuum pressure within said housing effecting expansion of said gloves at said hand hole means into said housing.

3. An apparatus as defined in claim 2 including means under the control of the user to activate and deactivate said vacuum pressure.

4. An apparatus as defined in claim 2 wherein said frame means is provided with abutment means adjacent each aperture in said frame means and each of said gloves is provided with a raised bead at the cuff of said glove with said raised bead being temporarily held by one of said abutment means.

5. An apparatus as defined in claim 4 wherein said abutment means comprises a ring member surrounding each aperture in said frame means.

6. A method of dispensing rubber gloves from an apparatus provided with hand hole means for the insertion of the hands of a user, said method comprising the steps of:
    a. retaining gloves at regularly spaced locations along a web material, said web material having an aperature at the locus of retainment of said gloves,
    b. covering said gloves with a packaging film that is lightly perforated at the locus of attachment of said gloves, c. periodically feeding said web material in order to position one of said gloves in registry with one of said hand holes,
d. expanding said glove with a vacuum pressure whereby said glove expands into said apparatus,
e. and removing said glove from its retained position by insertion of the hands of a user into said glove.

7. A method of dispensing rubber gloves as claimed in claim 6 including the additional step of feeding two webs in parallel wherein one of said webs retains right handed gloves and the other of said webs retains left handed gloves.

8. A method of dispensing rubber gloves as claimed in claim 6 including the additional steps of providing a raised bead at the cuff of said gloves and securing a ring member to said web material with said ring member providing a temporary stop abutment for one of said gloves.

9. A method of dispensing rubber gloves as claimed in claim 8 including the additional step of separating the raised bead at the cuff of said glove from the temporary stop abutment provided by said ring member by a twisting motion of the wrist of the user.

10. A method of dispensing rubber gloves as claimed in claim 6 including the additional step of providing said vacuum from a vacuum pump located within said apparatus.

11. A method of dispensing rubber gloves as claimed in claim 6 including the additional step of providing said vacuum from a central vacuum source.

* * * * *